(12) United States Patent
Suda

(10) Patent No.: US 7,758,504 B2
(45) Date of Patent: *Jul. 20, 2010

(54) ELECTRONIC DEVICE FOR HEALTH INDEX MEASUREMENT AND CONTROL METHOD OF THE SAME

(75) Inventor: Eikichi Suda, Kitagunma-gun (JP)

(73) Assignee: Nihon Seimitsu Sokki Co., Ltd., Kitagumma-gun (JP)

( * ) Notice: Subject to any disclaimer, the term of this patent is extended or adjusted under 35 U.S.C. 154(b) by 40 days.

This patent is subject to a terminal disclaimer.

(21) Appl. No.: 12/000,256

(22) Filed: Dec. 11, 2007

(65) Prior Publication Data

US 2009/0018402 A1    Jan. 15, 2009

Related U.S. Application Data

(63) Continuation of application No. 10/666,548, filed on Sep. 22, 2003, now Pat. No. 7,361,142.

(30) Foreign Application Priority Data

Sep. 20, 2002   (JP)   ............................. 2002-274792
Aug. 28, 2003   (JP)   ............................. 2003-209399

(51) Int. Cl.
    *A61B 5/00*   (2006.01)
(52) U.S. Cl. .................................................... 600/300
(58) Field of Classification Search ................. 600/300
    See application file for complete search history.

(56) References Cited

U.S. PATENT DOCUMENTS

| 3,690,313 | A | 9/1972 | Weppner et al |
| 4,531,526 | A | 7/1985 | Genest |
| 5,092,330 | A | 3/1992 | Duggan |
| 5,113,868 | A * | 5/1992 | Wise et al. ................... 600/488 |
| 5,865,733 | A | 2/1999 | Malinouskas et al. |
| 6,236,888 | B1 | 5/2001 | Thompson |
| 6,326,884 | B1 | 12/2001 | Wohlrabe |
| 6,494,829 | B1 * | 12/2002 | New et al. .................... 600/300 |
| 6,893,396 | B2 | 5/2005 | Schulze et al. |
| 7,361,142 | B2 * | 4/2008 | Suda ........................... 600/300 |
| 2004/0127811 | A1 | 7/2004 | Higuchi |

FOREIGN PATENT DOCUMENTS

| EP | 0 979 053 | 4/1998 |
| WO | WO-98/47423 | 10/1998 |

\* cited by examiner

*Primary Examiner*—Patricia C Mallari
*Assistant Examiner*—Karen E Toth
(74) *Attorney, Agent, or Firm*—Merek, Blackmon & Voorhees LLC; Catherine M. Voorhees

(57) ABSTRACT

The present invention allows easily performing various types of controls and improving productivity without adding a special communication section. The present invention includes a power receiving section 21 to be connected to a driving power supply 50, a voltage measuring section 22 configured to measure a variation of a power supply voltage that is inputted to the power receiving section 21, a signal extracting section 23 configured to analyze measured data thereof and to extract a digital code contained in the measured data, and a control section 24 configured to perform a specific control based on the extracted digital code. As the specific control, the control section 24 selects an operation mode corresponding to the digital code from selectively executable plural operation modes, performs a function setting corresponding to the digital code, or writes the digital code as individual information into a nonvolatile memory.

10 Claims, 6 Drawing Sheets

ELECTRONIC DEVICE FOR HEALTH INDEX MEASUREMENT AND CONTROL METHOD OF THE SAME

BACKGROUND OF THE INVENTION

1. Field of the Invention

The present invention relates to an electronic device for measuring a health index (also called as vital information) that is mainly a blood pressure or the like, and a control method of the electronic device under special circumstances.

2. Description of the Related Art

As an example of the electronic device for health index measurement of this type, a case of an electronic blood pressure meter will be explained. In recent years, it has become essential for the electronic blood pressure meter, being accompanied by increase of its performance, to be set to a dedicated operation mode for adjustment or inspection during a manufacturing process, an inspection process, or maintenance besides a normal operation. An example of the dedicated operation mode is a pressure display mode (a test mode to conduct the pressure display only) that is used when conducting a pressure inspection.

By the way, switching from a normal pressure measurement mode to a test mode for example should be easily set during a manufacturing process, an inspection process, or maintenance, but then it is needed not to be easily set to such a mode during a normal using state (a state that it is used in a normal blood pressure measurement mode). In other words, it is needed that an accidental switch of setting should not occur during normal use.

Consequently, the test mode is conventionally configured to start up, for example, when the following operations are carried out, which are normally impossible to happen.

(1) Long Pressing of a Particular Operating Switch Method:

In this method, as shown in FIG. 6, the test mode starts up when a power switch is pressed for a predetermined time T or longer.

(2) Special Operation of an Operating Switch Method:

In this method, as shown in FIG. 7, the test mode starts up when a particular operating switch A is operated for the predetermined number of times ("n" times) within a predetermined time T.

(3) Simultaneous Operation of Plural Operating Switches Method:

In this method, as shown in FIG. 8, the test mode starts up when operating switches A and B are simultaneously operated.

(4) Operation in a Particular Operating State Method:

In this method, as shown in FIG. 9, the test mode starts up when its power is turned ON in a state that an operating switch A is turned ON.

(5) Combination of the Above Method:

In this method, as shown in FIG. 10, the test mode starts up when its power is turned ON in a state that operating switches A and B are simultaneously turned ON and being kept on for a predetermined time T or longer.

However, all of these conventionally adopted methods (1) to (5) are focused on preventing a misoperation in a general using state, so that a demand for "easy switching" during a manufacturing process, an inspection process, or maintenance has been sacrificed.

Meanwhile, on many of blood pressure meters in recent years, the number of operating switches is reduced to minimum for an easiness of operation or cost reduction. For example, there is a model that uses one switch both as a power ON/OFF switch and a measurement start/stop switch. In a case of such model, it is practically impossible to adopt the above-described method (3) that is a combinatorial operation of plural operating switches. Therefore, for switching to the test mode, this model has no choice but to adopt the method (1) of long pressing operation or the method (4) of synchronous operation in a particular timing. However, while there is no problem for switching to one test mode, it is necessary to have a highly complicated operation for switching to other plural operation modes, or it has to abandon the switching itself to such plural operation modes. Specifically, in many cases, it is not possible to realize, due to the restriction on the number of switches, an attempt of providing the plural operation modes other than a normal operation mode, or a need of plural separate operations in an operation mode other than the normal operation mode.

In addition, the switching operation of operation modes needs to be performed on each one of manufactured products separately, so that, for example, when the long pressing of an operating switch method (1) is adopted, with the test mode being set to start up by pressing a power switch for two seconds, the switching operation of the operation mode on 50 of blood pressure meters takes 2 seconds×50=100 seconds at the minimum. Therefore, it has been a contributing factor to decrease production efficiency in a case of a pressure inspection process or the like for inspecting plural manufactured products all at once.

Consequently, to solve these disadvantages, such a method is devised that a connection terminal for testing is provided on the body of a blood pressure meter, and a dedicated device is externally connected to this terminal. However, while this method allows many testing operations to be easily performed externally, it includes a demerit of causing a complication of the structure and a cost increase since the dedicated connection terminal is newly provided on the body of the blood pressure meter.

In addition, besides these problems about the switching of the operation mode, there have been other problems as follows.

Conventionally, when an individual function setting is respectively performed on separate devices, function selection circuits are provided on electronic circuits of these devices, and the function setting is performed by switching switches or jumper lines. Otherwise, the individual function setting is carried out by writing a program into a nonvolatile memory. However, in many cases, these methods have a restriction that they can only be implemented in limited processes in a manufacturing stage and of course not after completion of the product.

Also, in recent years, as a technique for recording individual information in separate devices (for example, a serial number, information of a place of destination, and so forth), this information is recorded as electrical information in a nonvolatile memory or the like, and the opportunity of using this information for automation of maintenance or the like is increasing. However, when such individual information is to be recorded, it is impossible to write into a nonvolatile memory at a finishing stage of a product without connecting a dedicated communication circuit externally, which results in causing decrease in production efficiency. In addition, it is needless to mention that addition of a dedicated communication port causes complication of the structure and a cost increase.

As described above, it is conventionally required a lot of time and labor for switching the setting to an operation mode other than the normal mode such as the test mode for example, which causes a problem of low production efficiency when inspecting a large number of devices all at once. In addition, the restriction in inputting or changing individual information or the like also causes the problem of low production efficiency.

SUMMARY OF THE INVENTION

The present invention eliminates the above-described problems, and an object thereof is to provide an electronic device for health index measurement that allows easily performing various types of external controls without adding a special communication section (communication terminal, communication circuit, or the like), simultaneously controlling plural electronic devices, and externally inputting and changing individual information or the like easily to thereby improve production efficiency, and a control method in special cases for the same.

An electronic device of an invention of claim 1 comprises a power receiving section to be connected to a driving power supply, a voltage measuring section configured to measure a variation of a power supply voltage that is inputted to the power receiving section, a signal extracting section configured to analyze measured data thereof and to extract a specific signal contained in the measured data, a control section configured to perform a specific control based on the signal extracted by the signal extracting section.

In the present invention, a power supply line is used as a communication line, and a signal is incorporated as a voltage variation pattern in a power supply voltage, so that the electronic device can be externally controlled by the signal. Therefore, without adding a special communication section, various types of external controls can be easily performed, and a simultaneous control of plural electronic devices becomes possible. In addition, an external input and change of individual information or the like can be easily performed, and consequently, productivity thereof can be drastically improved.

As in claim 2, the second control section has a control function of controlling the voltage measuring section, the signal extracting section and the first control section to operate and perform a specific control only when the switch section is in a predetermined set state, whereby it is not necessary to always supply power to them, and it becomes possible to reduce power consumption.

As in claim 3, the first control section has a function of performing a kind of control selected from plural kinds of specific controls when receiving a specific signal from the signal extracting section, and the second control section has a function of selecting a kind of control to be performed in the first control section in accordance with which switch section of the plural switch sections is operated and having it executed, whereby it becomes possible to perform plural specific controls by one kind of signal.

Moreover, as in claim 4, the second control section has a function capable of selecting and executing one kind of operation mode, or two or more kinds of operation modes as an operation mode of this electronic device, and has a function of operating the voltage measuring section, the signal extracting section and the first control section to make them perform the specific control only when a specific operation mode is selected out of these operation modes, whereby power consumption can be reduced as in claim 2.

As in claim 5, the second control section has a function capable of selecting and executing one kind of operation mode, or two or more kinds of operation modes as an operation mode of this electronic device, and has a function of selecting a kind of control to be performed in the first control section in accordance with which operation mode of these operation modes is selected and having it executed, whereby it becomes possible to perform plural specific controls by one kind of signal.

The signal is preferably given as a specific time-series variation (pattern), which does not affect the operation of the electronic device, and is not generated under a normal using state for preventing a misoperation. In an invention of claim 6, the signal is given as a time-series variation of a power supply voltage within a range that assures a normal operation of the electronic device.

Moreover, as the specific control performed by the control section, various types of controls are conceivable. In an invention of claim 7, as the specific control, the control section selects a specific operation mode corresponding to the signal extracted by the signal extracting section from selectively executable plural operation modes. Accordingly, the plural operation modes can be selectable by preparing plural time-series variation patterns to be given to the power supply voltage for instance.

Moreover, in an invention of claim 8, as the specific control, the control section performs a specific function setting corresponding to the signal extracted by the signal extraction section.

Moreover, in an invention of claim 9, as the specific control, the control section performs writing of the signal extracted by the signal extracting section as individual information into a nonvolatile memory. Here, representative examples of the individual information are a serial number and information of a place of destination.

Moreover, in an invention of claim 10, as the specific control, the control section performs writing of an operation program that is given by the signal extracted by the signal extracting section into a nonvolatile memory.

A control method of an electronic device of an invention of claim 11 comprises connecting a driving power supply to the power receiving section of the electronic device for health index measurement described in any one of claims 1 to 10, and applying from the power supply to the power receiving section of the electronic device a power supply voltage in which a digital code of a voltage variation pattern that is a combination of a high-level and low-level voltages is incorporated so that the electronic device performs a specific control based on the digital code.

Accordingly, with the signal as a digital code being incorporated in the power supply voltage, extracting of a specific signal can be easily performed only by adopting an A/D converter in the voltage measuring section. Consequently, an external control according to the digital code becomes possible using a power supply line as a communication line without adding a special communication section. In addition, a simultaneous control of plural electronic devices also becomes possible, so that productivity thereof can be drastically improved.

In the control method of an invention of claim 12, in claim 11, the driving power supply has a function for selectively incorporating any one of plural digital codes in the power supply voltage, and the electronic device performs a control corresponding to the incorporated digital code. Accordingly, various types of external controls can be easily performed.

In the control method of an invention of claim 13, in claim 11, the driving power supply has a function for incorporating an inputted optional digital code to the power supply voltage, and the electronic device performs a control corresponding to the incorporated digital code. Accordingly, registering individual information such as a serial number and the like to the electronic device and setting an individual function to the electronic device can be easily performed.

In the control method of an invention of claim 14, in any one of claims 11 to 13, the driving power supply sets a low level voltage period with a predetermined length before an incorporating period of the digital code, the low level voltage being higher than the minimum operating voltage of the electronic device, and after the low level voltage period, the digital code that begins with a high level voltage is incorporated.

Accordingly, by providing the predetermined low level voltage period before the incorporating period of the digital code, a malfunction due to an initial voltage drop can be prevented. Specifically, the low level is retained for a predetermined period of time, and further, the digital code is formed on an increase side of a voltage, so that if a rapid voltage drop or a chattering of the voltage occurs just after turning on the power particularly when an AC adapter or the like is used for the power supply, an accidental false recognition of the digital code does not happen, thereby allowing a reliable control.

DETAILED DESCRIPTION OF THE PREFERRED EMBODIMENT

Hereinafter, an embodiment of the present invention will be explained based on the drawings.

Figure 1:
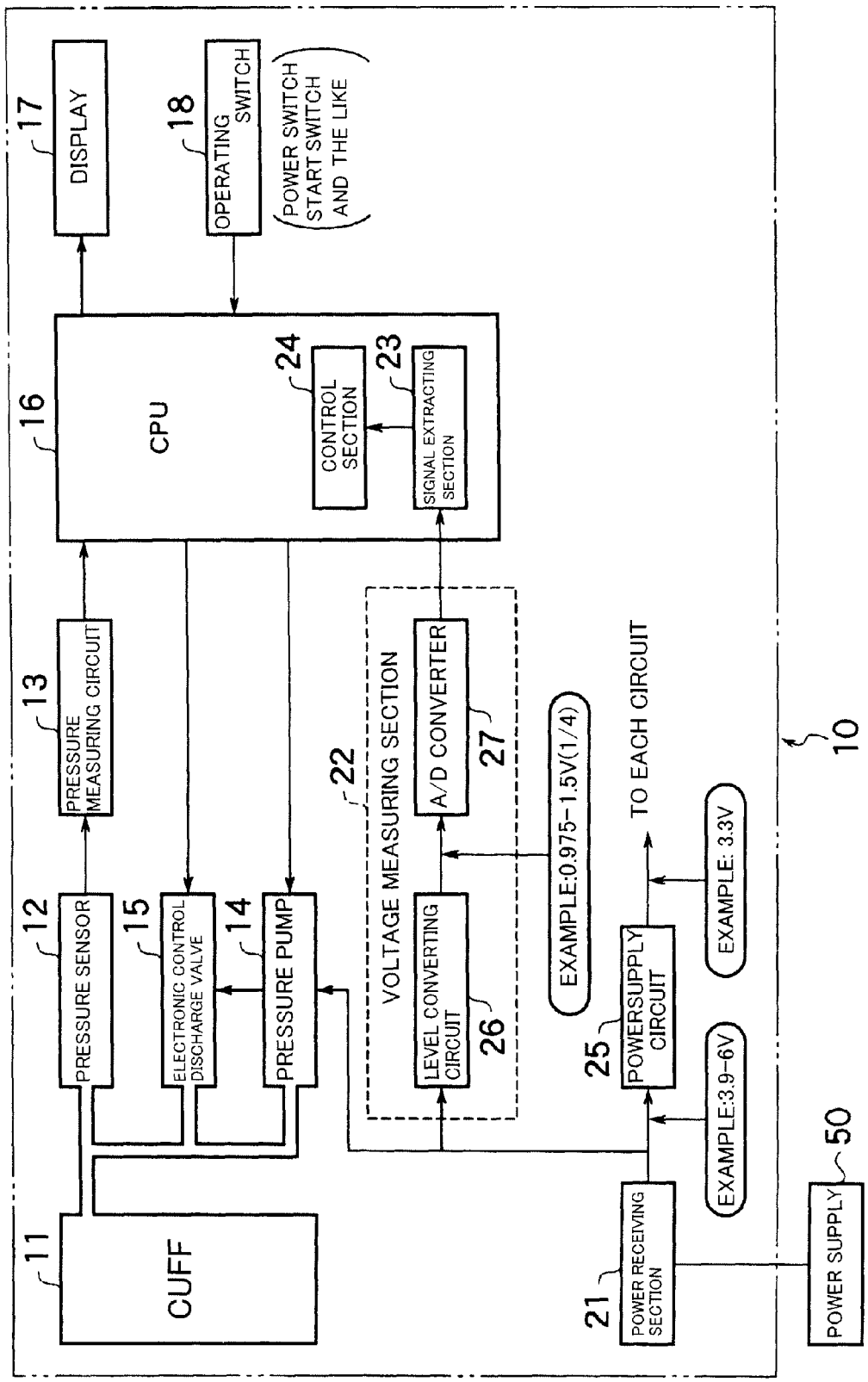
FIG. 1 is a block diagram showing a configuration of an embodiment of the present invention.

FIG. 1 is a block diagram showing an electronic blood pressure meter 10 as an electronic device of the embodiment. As basic components for blood pressure measurement, this electronic blood pressure meter 10 includes a cuff 11 for wrapping an artery passage portion (measuring portion) such as an upper arm or a wrist of a person to be measured, a pressure sensor 12 and a pressure measuring circuit 13 for detecting the pressure inside the cuff 11, a pressure pump 14 for introducing pressurized air into the cuff 11, an electronic control valve 15 for discharging the pressurized air inside the cuff 11, a CPU (control device) 16 (second control section) for performing various types of controls, a display 17 such as a liquid crystal display, and operating switches 18 such as a power switch, a start switch and the like. The blood pressure meter 10 measures a blood pressure from a variation of the inner pressure of the cuff 11, the variation being generated through a process including wrapping the measuring portion such as an upper arm or a wrist or the like by the cuff 11, introducing pressurized air into an airbag inside the cuff 11 to stop the blood flow to the peripheral portion once by pressing the measuring portion, and thereafter, gradually decreasing the inner pressure inside the cuff 11.

Here, the pressure sensor 12 outputs a pulse whose frequency varies according to the pressure value inside the cuff 11, and the pressure measuring circuit 13 converts the output of the pressure sensor 12 into a digital value and inputs it to the CPU 16. Incidentally, in a case of a one-chip CPU, the pressure measuring circuit 13 can be constructed by an internal circuit and software. The pressure pump 14 carries out a function for increasing the inner pressure of the cuff 11 to a predetermined pressure by a control from the CPU 16. By a control from the CPU 16, the electronic control discharge valve 15 works to decrease (discharge) the inner pressure of the cuff 11 by a constant speed during a blood pressure measurement, and to rapidly decrease the inner pressure after the measurement is completed. The CPU 16 controls all the processes of the blood pressure measurement operation based on an operation program stored in advance.

Besides these basic components for blood pressure measurement, the blood pressure meter 10 includes a power receiving section 21 to be connected to a driving power supply 50, a voltage measuring section 22 configured to measure a variation of a power supply voltage that is inputted to the power receiving section 21, a signal extracting section 23 configured to analyze the measured data and to extract a specific signal contained in the measured data, a control section 24 (first control section) configured to perform a specific control based on the signal extracted by the signal extracting section 23, and a power supply circuit 25 configured to supply power with necessary voltage from the supplied voltage to each circuit.

The power receiving section 21 includes a power supply connecting terminal such as a battery terminal or an AC adapter jack for example. The power measuring section 22 includes a level converting circuit 26 and an A/D converter 27. The level converting circuit 26 is a one called as attenuator, and carries out a function for converting a power supply voltage that is supplied to the blood pressure meter 10 to a possible input level of the A/D converter 27. Incidentally, when the power supply voltage supplied in advance is at the possible input level of the A/D converter 27, the level converting circuit 26 can be omitted. The A/D converter 27 performs A/D conversion of the power supply voltage value supplied to the blood pressure meter 10 by a predetermined time period Ts that is faster than a time-series variation contained in the power supply voltage, and inputs the converted power supply voltage value to the CPU 16. This A/D converter 27 can also be internally constructed when the one-chip CPU is adopted.

The signal extracting section 23 analyzes a time-series variation pattern contained in the supplied power supply voltage from time-series measured data of the power supply voltage supplied to the blood pressure meter 11 to thereby extract a digital code. When a digital code is detected, the digital code is inputted to the control section 24. The control section 24 performs a control corresponding to the digital code sent from the signal extracting section 23. This control includes ① selection and execution of an operation mode (including a test mode for example), ② setting of an individual function, ③ writing of an individual information such as a serial number or the like, ④ writing of a program, and so forth. Here, the signal extracting section 23 and the control section 24 are realized mainly by software of the CPU 16.

Next, a method for performing an external control using a power supply line will be explained.

To perform the external control of the electronic blood pressure meter 11, a time-series variation pattern is given to the power supply voltage that is supplied to the electronic blood pressure meter 11 by a dedicated external device (considered to be contained in the power supply 50 in the configuration shown in FIG. 1). In this case, the power supply voltage containing the time-series variation pattern can be supplied individually to a single blood pressure meter 11, or supplied simultaneously to plural blood pressure meters.

Figure 2:
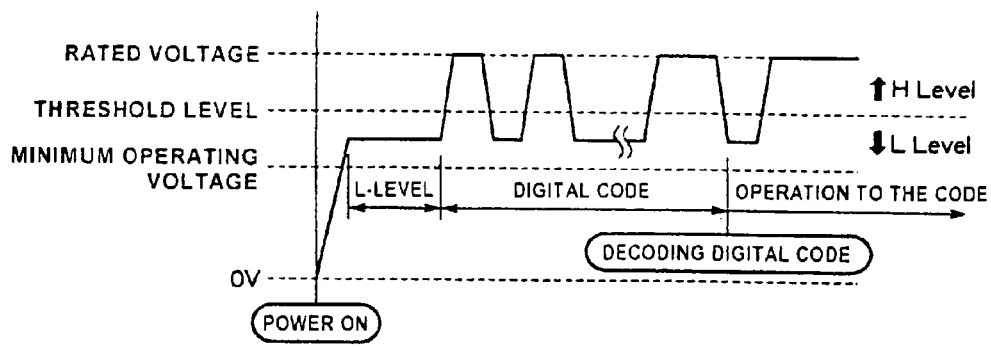
FIG. 2 is an explanatory view of the present invention showing an example of a variation pattern of a power supply voltage.

FIG. 2 is a view showing the variation of the power supply voltage in which a digital code is incorporated. The power supply voltage is retained between the minimum operating voltage that assures a normal measuring operation of the electronic blood pressure meter 10 and a rated voltage, and a time-series voltage variation pattern corresponsive to the digital code is incorporated in the power supply voltage therebetween. Specifically, the digital code is incorporated in a pattern of rising and falling between an H-level and an L-level having a threshold level at the center. When the power supply 50 capable of incorporating such a digital code is connected to the power receiving section 21 of the electronic blood pressure meter 10, power supply voltage data are A/D converted by the A/D converter 26 at a predetermined interval of time and are inputted to the signal extracting section 23. The signal extracting section 23 analyzes the inputted data based on the threshold level that is provided in advance, judges whether it is high-level (H) or low-level (L), and extracts a digital code composed of a high and low combination when the digital code is incorporated therein. Incidentally, the H-level and the L-level corresponsive to the digital code and the threshold level that is a judging standard thereof are set to appropriate values to surely take effect within the range of an operable power supply voltage for the electronic blood pressure meter 10.

Here, for preventing a malfunction due to an initial voltage drop, there is provided a time period (low level voltage period) to surely retain the L-level for a predetermined period before incorporating a digital code, and after the time period, a digital code that begins with a high level voltage is incorporated. Accordingly, if a rapid voltage drop or a chattering of the voltage occurs just after turning on the power particularly when an AC adapter is used for the power supply, an accidental false recognition of the digital code does not happen.

Incidentally, FIG. 2 is showing a case of inputting the digital code just after the power is turned on, but also in a case of inputting the digital code in a state that the power is already turned on, a good way to prevent a false recognition is to decrease the power supply voltage to the L-level once, retain the L-level period for a predetermined time, and input the digital code that begins with a high level voltage. In addition, by adding an error detecting code such as a checksum to the digital code, reliability of the communication can be further increased.

Figure 3:
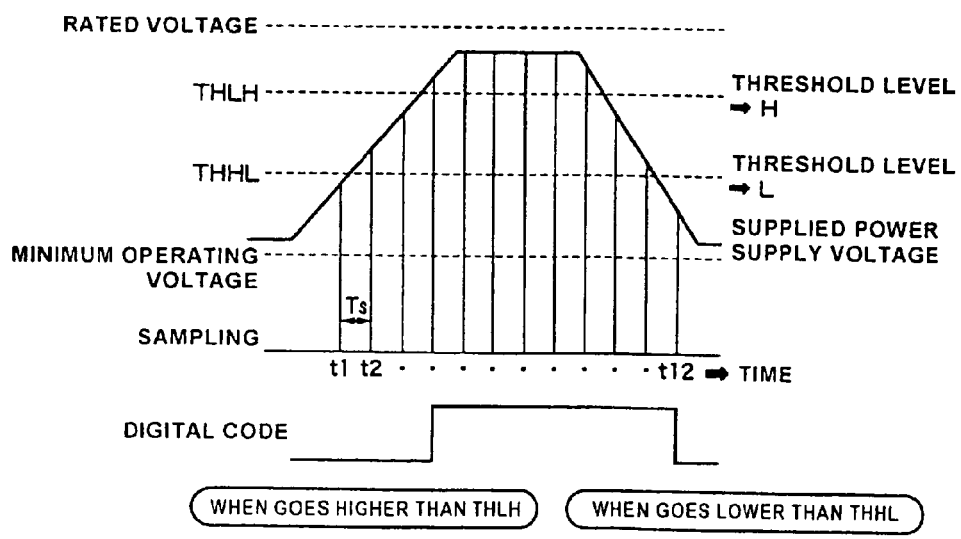
FIG. 3 is an explanatory view of the present invention showing a relationship between a variation of a supplied power supply voltage and a digital code.

FIG. 3 is a view showing a concrete example of a method for judging high and low of the power supply voltage and the digital code. In this example, in the signal extracting section 23, a first threshold level THLH for judging a variation from the low level (L) to the high level (H), and a second threshold level THHL for judging a variation from the high level (H) to the low level (L) (Note: THLH>THHL) are set in advance, where sampling data are judged as either high or low based on these threshold levels THLH and THHL. For example, the data is judged as high (H) when it goes higher than the THLH from the downside of the THLH, and the data is judged as low (L) when it goes lower than the THHL from the upside of the THHL. Accordingly, reliability of judging signal improves.

In either case, when one or more digital code is extracted from the supplied power supply voltage, the control according to the digital code is performed. For example, when plural operation modes are registered in advance, an operation mode is set according to the digital code.

Figure 4:
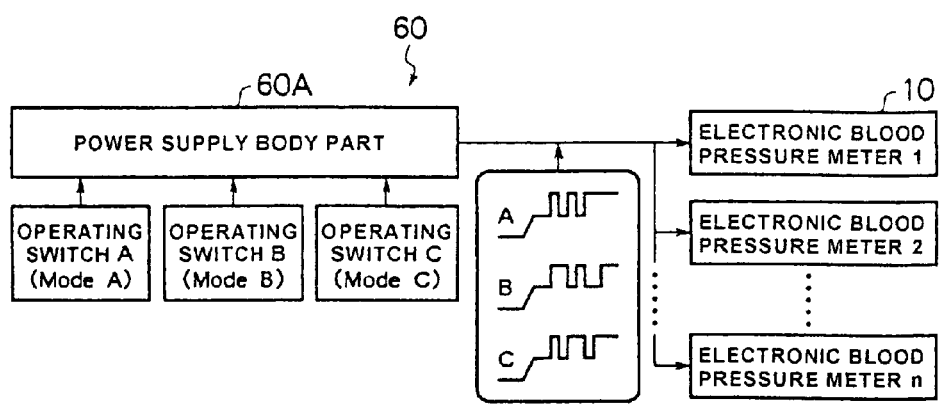
FIG. 4 is an explanatory view of the present invention showing a configuration for simultaneously switching operation modes of plural electronic blood pressure meters by a power supply capable of inputting plural digital codes.

FIG. 4 is showing an example of performing a switching of operation mode by an external control. On a body part 60A of a power supply 60 capable of outputting a digital code, there are provided three types of operating switches A to C, and by operating the operating switches A to C, three types of digital code patterns A to C can be incorporated separately in a power supply voltage. For example, when the operating switch A is operated, a digital code of pattern A is outputted, when the operating switch B is operated, a digital code of pattern B is outputted, and when the operating switch C is operated, a digital code of pattern C is outputted.

When this power supply 60 is connected to the electronic blood pressure meter 10 and any one of the operating switches A to C is operated, one digital code from predetermined patterns A to C corresponding to this operation can be inputted to the electronic blood pressure meter 10. Therefore, when an operation mode corresponding to the digital code is registered in the electronic blood pressure meter 10, this operation mode can be automatically started up only by connecting the power supply 60. For example, when a test mode is registered in advance and a digital code for instructing the test mode is incorporated in the power supply voltage, the test mode can be started up only by connecting the power supply 60. In this way, since other complicated operations are unnecessary, the same operation mode can be easily and simultaneously set to a plurality of the electronic blood pressure meter 10. In addition, by registering plural operation modes besides the normal operation mode in the electronic blood pressure meter 10, its setting can be switched to any one of these operation modes.

Moreover, by using a power supply having plural output sections independent to one another and being capable of outputting individual digital codes to each of the output sections, it is possible to set an individual operation mode on each of the electronic blood pressure meters which is connected to each of the output sections.

Moreover, when a personal computer having a dedicated software for externally controlling the electronic blood pressure meter is connected to the body part of the power supply, and it is configured that an arbitrary digital code can be inputted from the personal computer, it is possible to make the electronic blood pressure meter to perform various types of controls by, for example, changing the software in the personal computer without requiring to change the main part of the power supply.

Figure 5:
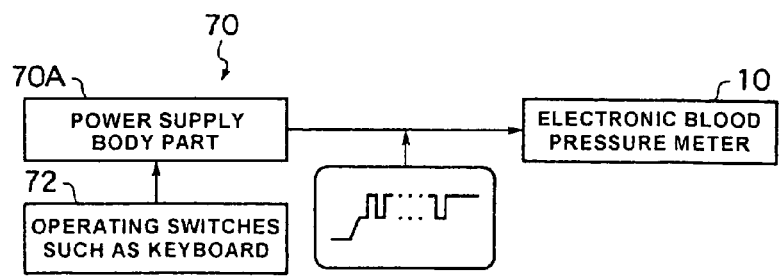
FIG. 5 is an explanatory view of the present invention showing a configuration for writing a serial number into an electronic blood pressure meter by a power supply capable of inputting an optional digital code by an operation of a keyboard.
Figure 6:
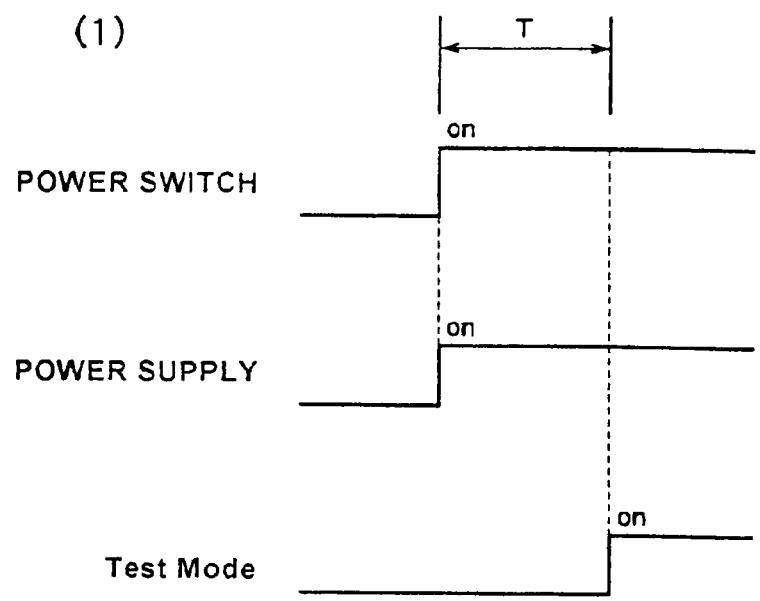
FIG. 6 is an explanatory view showing a first conventional operation example for starting up a test mode.
Figure 7:
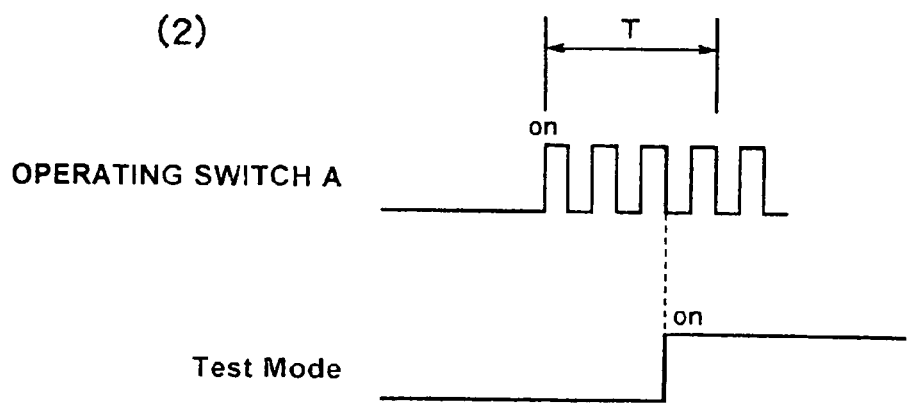
FIG. 7 is an explanatory view showing a second conventional operation example for starting up the test mode.
Figure 8:
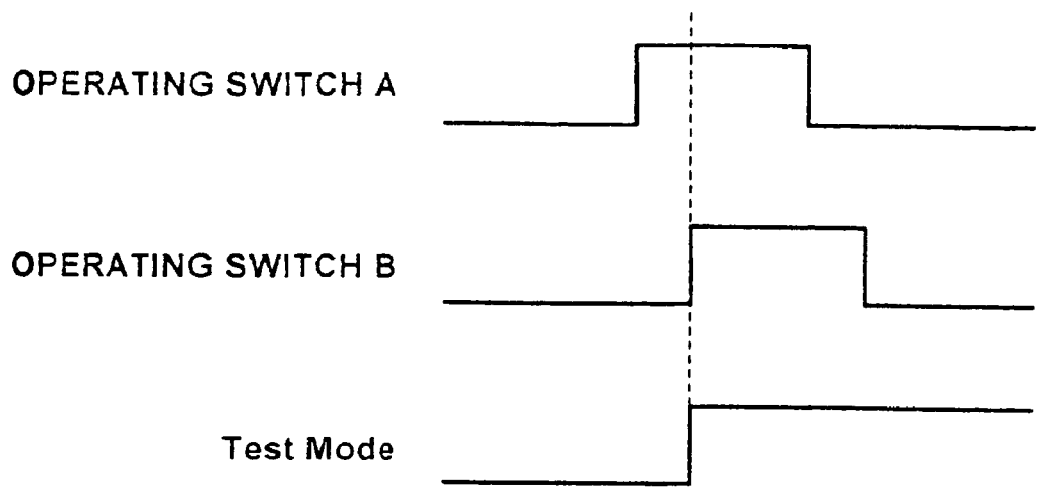
FIG. 8 is an explanatory view showing a third conventional operation example for starting up the test mode.
Figure 9:
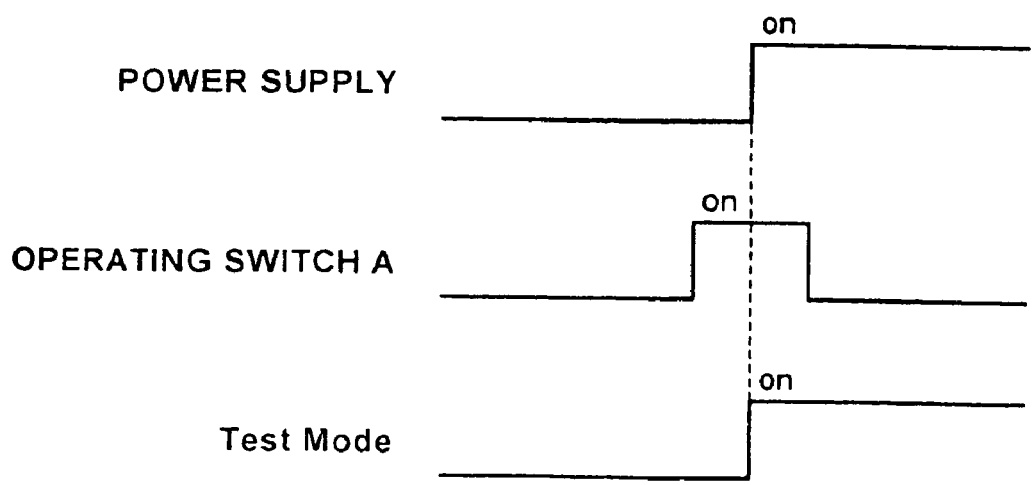
FIG. 9 is an explanatory view showing a fourth conventional operation example for starting up the test mode.
Figure 10:
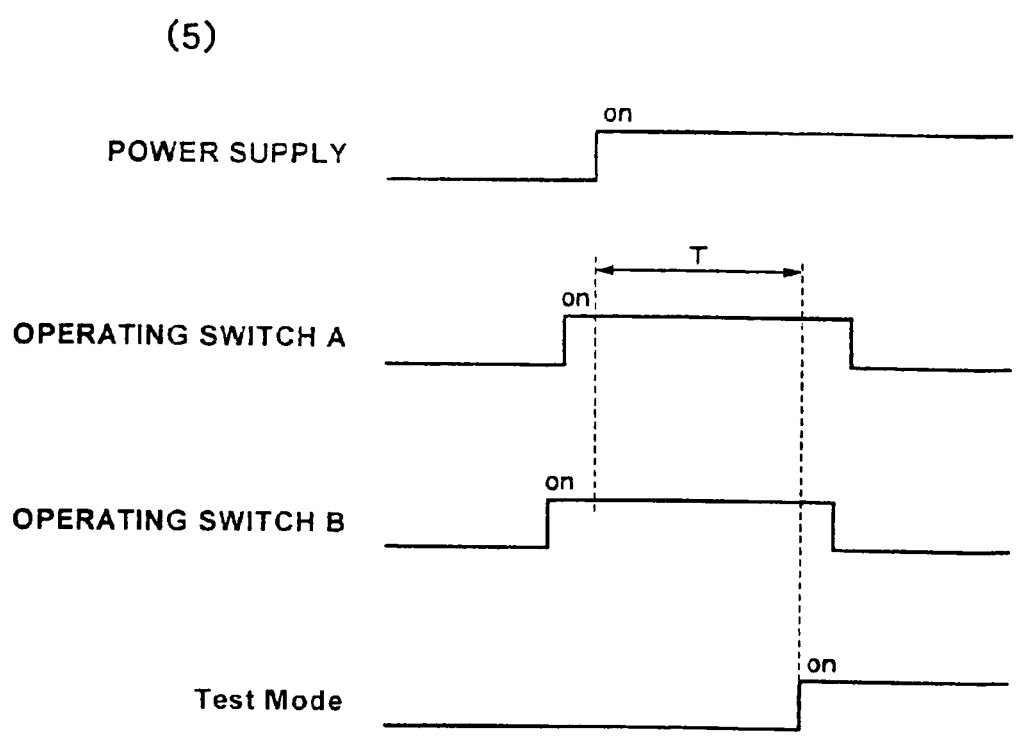
FIG. 10 is an explanatory view showing a fifth conventional operation example for starting up the test mode.

Moreover, as shown in FIG. 5, when operating switches 72 such as a keyboard for externally controlling the electronic blood pressure meter is connected to a body part 70A of a power supply 70 and an arbitrary digital code can be inputted from the operating switches 72 such as a keyboard, it is possible to make the electronic blood pressure meter 10 to perform various types of controls, for example, according to an inputted digital code from the operating switches 72 such as a keyboard without requiring to change the main part of the power supply.

For example, by outputting a digital code pattern corresponding to the operation of the operating switches 72 such as a keyboard from the output section of the power supply 70, it is possible to set an individual function to each electronic blood pressure meter 10, or to write individual information such as a serial number, information of a place of destination, and so forth into a nonvolatile memory inside the electronic blood pressure meter 10. Consequently, even after completion of the product, setting/changing of the individual function or writing/changing of the individual information such as a serial number and so forth becomes possible.

Moreover, a measurement program can be registered or changed in the electronic blood pressure meter 10 by inputting the digital code. For example, it can be used for inputting or changing the measurement program in a portable electronic blood pressure meter, which performs the measurement of blood pressure at predetermined intervals of time based on the measurement program inputted in advance, memories the results, and thereafter analyzes a diurnal variation of the blood pressure value or the like.

Moreover, a portable electronic blood pressure meter of this type divides a time period up to 24 hours (one day) or 48 hours (two days) at the maximum into plural time period blocks (a daytime period and a nighttime period for example), and sets a measurement intervals (time intervals) in each of the time periods in order to observe the diurnal blood pressure variation of a subject. This portable electronic blood pressure meter automatically performs the blood pressure measurement at predetermined intervals of time based on a "measurement program" inputted in advance to designate time periods and measurement intervals. Generally, a portable blood pressure meter of this type is used in a combination of a body of the blood pressure meter and an analysis device. The analysis device is a device for inputting the measurement program to the blood pressure meter or for extracting a measured result stored in the blood pressure meter from the blood pressure meter and analyzing the measured result, and is configured with a dedicated machine or a personal computer having dedicated software, and a dedicated interface device that connects the analysis device and the body of the blood pressure meter. In this case, a communication line between the analysis device and the body of the blood pressure meter needs to be a duplex specification. When the present invention is implemented on the program input from the analysis device to the body of the blood pressure meter, the communication line between the analysis device and the body of the blood pressure meter can be a simplex of output only. Since a dedicated duplex line is conventionally used for the communication with the analysis device, the implementation of the present invention making this line simplex can contribute to decrease the cost.

Incidentally, while the above embodiment explains a case that, when switching the operation mode, the mode switching of the electronic blood pressure meter is performed automatically only by inputting the digital code from the power supply, it may also be configured to perform the mode switching by a combination of the digital code input and other operations. This point similarly applies to the function setting, the individual information writing, and the like.

Moreover, the CPU 16 (the second control section) for performing various kinds of controls is configured to have a control function of controlling the voltage measuring section 22, the signal extracting section 23, and the control section 24 (the first control section) for performing a specific control to operate and perform a specific control only when the switch section such as the operating switch 18 is in a predetermined set state, whereby it is not necessary to always supply power to them, and it becomes possible to reduce power consumption.

Moreover, the control section 24 (the first control section) for performing the specific control is configured to have a function of performing a kind of control selected from plural kinds of specific controls when receiving a specific signal from the signal extracting section 23, and the CPU 16 (the second control section) for performing various kinds of controls is configured to have a function of selecting a kind of control to be performed in the control section 24 (the first control section) in accordance with which switch section of plural switch sections such as, for example, the operation switch 18 is operated and having it executed, whereby it becomes possible to perform plural specific controls by one kind of signal.

Moreover, the CPU 16 (the second control section) for performing various kinds of controls is configured to have a function capable of selecting and executing one kind of operation mode, or two or more kinds of operation modes as an operation mode of this electronic device, and is configured to have a function of operating the voltage measuring section 22, the signal extracting section 23 and the control section 24 (the first control section) for performing the specific control to make them perform the aforesaid specific control only when a specific operation mode is selected out of these operation modes, whereby it becomes possible to reduce power consumption.

Moreover, the CPU 16 (the second control section) for performing various kinds of controls is configured to have a function of capable of selecting and executing one kind of operation mode, or two or more kinds of operation modes as an operation mode of this electronic device, and is configured to have a function of selecting a kind of control to be performed in the control section 24 (the first control section) in accordance with which operation mode of these operation modes is selected and having it executed, whereby it becomes possible to perform plural specific controls by one kind of signal.

In this case, the operation mode means the operation mode in which a specific pressure value is applied, or the operation mode in which the pressure is applied with a specific variation pattern, for example, in the case of a blood pressure meter. Or, it means the mode, in which the pressure value in a certain range is applied. Furthermore, it means the mode in which the pressure value applied to the blood pressure meter rises or lowers in a specific pressure range. Or, it means the mode in which the pressure value applied to the blood pressure meter changes at a rising speed or a lowering speed in a certain range.

As described above, the control with use of the operation modes can be effectively utilized on the occasion of an air leakage test of a blood pressure meter, for example. Namely, this test makes evaluation by connecting an air tank of a fixed capacity to the blood pressure meter, applying the pressure value corresponding to the maximum pressure indication value of the blood pressure meter after closing an exhaust valve, leaving this for a fixed time while monitoring the pressure indication value after stopping the pressure supply, and finding whether or not the pressure indication value lowers more than a predetermined range.

A concrete example, in which the method of performing a control by using the above-described operation modes is applied to the above-described test, is as follows. It is assumed to construct a system which performs the control such that "when a specific signal (pattern 1) is inputted at the time of the indicated pressure >10 mmHg, the exhaust valve is closed after air is evacuated for a fixed time," and "when the specific signal (pattern 1) is inputted at the time of the indicated pressure <10 mmHg, air is evacuated," for example. Thereupon, first, when the specific signal (pattern 1) is inputted in a state in which the applied pressure is 0 mmHg (not more than 10 mmHg), the exhaust valve of the blood pressure meter is closed after a lapse of a predetermined time, and when the specific signal (pattern 1) is inputted in the state until the applied pressure value reaches a predetermined pressure value (during pressurization), during the air leakage test with pressure supply being stopped, and after the air leakage test (10 mmHg or more in each state), the exhaust valve of the blood pressure meter is opened, and evacuation of air is performed.

Moreover, the system as follows is assumed. Namely, it is assumed to construct the system which performs the control such that "when the specific signal (pattern 1) is inputted at the pressure rising speed≠a predetermined rising speed range, air is evacuated and an alarm indication is performed" and "when the specific signal (pattern 1) is inputted at the pressure lowering speed≠a predetermined lowering speed range, air is evacuated and an alarm indication is performed." Thereupon, first, the specific signal (pattern 1) is inputted at each fixed interval, whereby in the case in which an extraordinary pressure rise caused by clogging in an air circuit, or insufficient pressure rising speed due to puncture of the air circuit occurs during a pressurizing operation, and when the predetermined signal (pattern 1) is inputted in the state in which the pressure rising speed deviates from the predetermined range, the test is stopped and air is evacuated, and the corresponding alarm indication is made.

Moreover, in a pressure lowering speed test and the like, when the predetermined signal (pattern 1) is inputted in the state in which the pressure value lowers at the air evacuating speed which deviates from the predetermined range during a constant-speed air evacuating operation, the test is stopped and air is evacuated, and the corresponding alarm indication is made. In this manner, a different operation control is made possible for each test state by one control signal pattern, as a result of which, the manufacturing facility can be simplified.

As has been described above, according to the present invention, the following advantages are achieved:

(1) A power input line is used as a control signal line, so that an external control of a device can be realized with low cost without having a dedicated communication line besides the power supply system. For example, when an A/D converter is used for battery remaining detection, a battery remaining detection circuit can be used as a voltage measuring section as it is, so that the external control of a device can be realized only by adding software;

(2) Since a special communication circuit is not required, it is not necessary to newly provide a connection port for communicating with an external device, so that complication of the structure and increase of the cost can be avoided;

(3) A power supply voltage itself is used as the control signal, so that it is not necessary to provide a complicated modulation circuit or a demodulation circuit such as a means for overlapping a high-frequency signal for example on both sides of sending and receiving the control signal. An input device of the control signal is simply achieved by installing a control circuit of output voltage in an external power supply device;

(4) It is possible to simultaneously control plural devices, so that, for example, a switching operation to a dedicated inspection mode for a pressure inspection process can be efficiently performed in a short period of time. In addition, an operation control according to actual inspection process becomes possible in a state that the setting is switched to the inspection mode, so that productivity can be drastically improved; and (5) Even after completion of the product, it is possible to set a function separately on each of the products and to set (write) individual information such as a serial number on each of the products. Accordingly, when manufacturing plural products of the same model but having different individual specifications, the products conventionally cannot be in a completed state until a final product specification is determined for each of the product, but when the present invention is used, the products can be in a completed state all at once even before the final product specification is determined, and thereafter, individual function setting and individual information registering can be performed, so that improvement of productivity can be expected.

What is claimed is:

1. An electronic device for health index measurement, comprising:
    a power receiving section that receives a power supply voltage, in which a digital code for performing a specific control is incorporated so that a low level voltage period of a predetermined length and higher than a minimum operating voltage of an electronic device is set before a period of incorporating the digital code, and said digital code begins with a high-level voltage after said low-level voltage period, and is expressed by a variation pattern of a combination of a high-level voltage and a low-level voltage;
    a voltage measuring section configured to measure a variation of a power supply voltage that is inputted to said power receiving section;
    a signal extracting section configured to analyze the measured variation of a power supply voltage and to extract said digital code contained in the measured variation; and
    a first control section configured to perform said specific control based on said digital code extracted by said signal extracting section.

2. An electronic device for health index measurement, according to claim 1, further comprising:
    a second control section configured to perform a control for health index measurement and other necessary controls; and
    a switch section configured to transmit a switching signal and other signals to each section by a predetermined setting operation,
    wherein said second control section has a control function of controlling said voltage measuring section, said signal extracting section and said first control section to operate and perform a specific control only when said switch section is in a predetermined set state.

3. An electronic device for health index measurement according to claim 1 further comprising:
    a second control section configured to perform a control for health index measurement and other necessary controls;
    wherein said second control section has a function capable of selecting and executing one kind of operation mode, or two or more kinds of operation modes as an operation mode of said electronic device, and has a function of operating said voltage measuring section, said signal extracting section and said first control section to make them perform said specific control only when a specific operation mode is selected out of these operation modes.

4. The electronic device for health index measurement according to claim 1, wherein said digital code is given as a time-series variation of a power supply voltage within a range that assures a normal operation of said electronic device.

5. The electronic device for health index measurement according to claim 1, wherein plural kinds of said digital code are prepared, said first control section has plural operation modes corresponding to the plural kinds of digital code, and selects and executes a specific operation mode corresponding to the kind of digital code extracted by said signal extracting section.

6. The electronic device for health index measurement according to claim 5, wherein the operation mode is a mode in which function setting is performed.

7. The electronic device for health index measurement according to claim 1, wherein said first control section has a function of writing said digital code extracted by said signal extracting section into a nonvolatile memory as individual information.

8. The electronic device for health index measurement according to claim 1, wherein said first control section has a function of writing an operation program that is given by said digital code extracted by said signal extracting section into a nonvolatile memory.

9. A control method of an electronic device for health index measurement, comprising:
    connecting a driving power supply for supplying the power supply voltage to said power receiving section of the electronic device for health index measurement according to claim 1; and
    applying from said power supply to said power receiving section of said electronic device a power supply voltage in which said digital code is incorporated, so that said electronic device performs a specific control based on the digital code.

10. The control method of the electronic device for health index measurement according to claim 9, comprising:
    said driving power supply for supplying the power supply voltage incorporating said digital code in said power supply voltage.

* * * * *